United States Patent [19]

Munsch

[11] 4,043,333

[45] Aug. 23, 1977

[54] CLAMP-ON INJECTION SITE

[75] Inventor: John Michael Munsch, Libertyville, Ill.

[73] Assignee: Baxter Laboratories, Inc., Deerfield, Ill.

[21] Appl. No.: 613,709

[22] Filed: Sept. 15, 1975

[51] Int. Cl.² .............................................. A61M 5/00
[52] U.S. Cl. ................................. 128/214 R; 128/2 F; 138/103
[58] Field of Search ........... 128/214 R, 214 C, 214 D, 128/214.2, 2 F; 138/103, 158, 161, 162

[56] References Cited

U.S. PATENT DOCUMENTS

| 3,327,709 | 6/1967 | Nehring et al. | 128/214 D |
| 3,447,570 | 6/1969 | Collins | 128/214 R X |
| 3,456,965 | 7/1969 | Gajewski et al. | 128/334 C X |
| 3,850,202 | 11/1974 | Morgan | 138/103 |

Primary Examiner—Dalton L. Truluck
Attorney, Agent, or Firm—George H. Gerstman; Paul C. Flattery

[57] ABSTRACT

A disposable self-locking injection site can be clamped onto tubing anywhere along the line. The injection site includes a tubular barrel having two sections integrally hinged together with snap-fitting coupler parts which lock the sections together in a closed position about the line. The tubular barrel is shaped to define an interior recess communicating with at least one needle-receiving aperture. The interior recess snugly receives a self-sealing needle-penetrable resilient member or sleeve for cushioning and fluidly sealing the line so as to permit fluid-tight injection and withdrawal of a needle.

17 Claims, 4 Drawing Figures

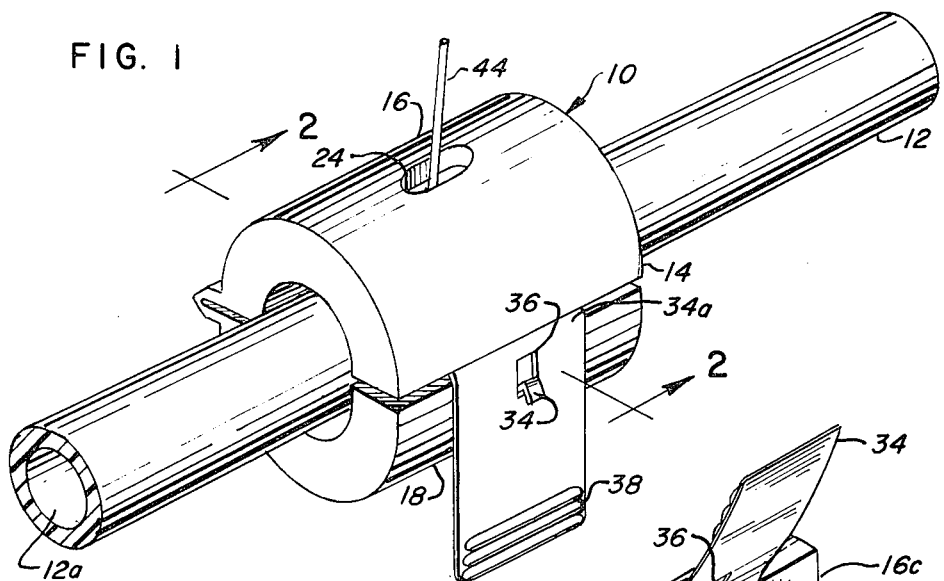
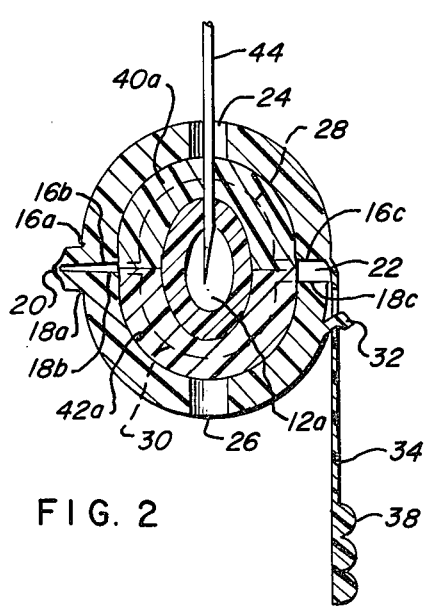
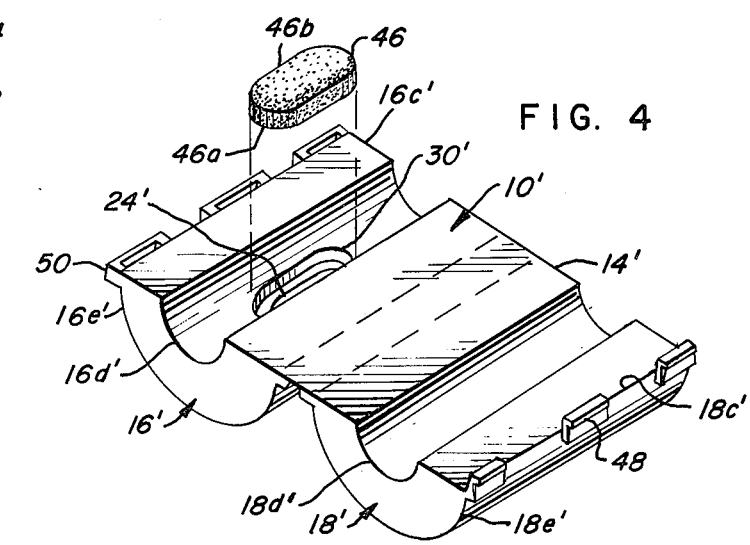

CLAMP-ON INJECTION SITE

BACKGROUND OF THE INVENTION

This invention relates to an injection site, and more particularly, to a needle-penetrable self-sealing device for the administration of injected fluids into a flow line.

It is often desirable to inject supplemental medicament into a needle-penetrable flow line. When the needle is inserted and withdrawn from the line, however, leakage often occurs. Such leakage is undesirable and may be detrimental to the patient's health.

In an effort to solve this problem, injection sites such as found in U.S. Pat. No. 3,447,570 and 2,832,338, have been connected to the flow line. When these flow lines have been stored and compressed for long periods of time, however, creep and set (bending and twisting) occur about the injection site, causing line leakage. Furthermore, the injection site described in U.S. Pat. No. 3,447,570 requires the injection site to be heat-sealed, sonic welded or adhesively bonded to the flow line, causing further assembly time and expense. The injection site described in U.S. Pat. No. 2,832,338 requires the flow line to be severed and physically separated for installation purposes.

It is therefore an object of this invention to avoid creep and set about an injection site.

Another object of this invention is to provide a self-clamping needle-penetrable tube sealer which prevents line leakage.

A further object of this invention is to provide a portable self-sealing injection site which can be clamped onto the tubing anywhere along the line.

It is still another object of this invention to provide a disposable injection site of simple design and construction, which is relatively inexpensive to manufacture, dependable in operation, readily installed and capable of performing properly without line leakage after long periods of use.

The foregoing and other objects and advantages will be apparent from the following description and appended claims taken in conjunction with the accompanying drawings.

SUMMARY OF THE INVENTION

In accordance with principles of the present invention, there is provided a self-clamping injection site adapted to be positioned along a flexible needle-penetrable tubular conduit. The self-clamping injection site includes sleeve means having first and second sections hinged together and operable between an open position for removable positioning along the tubular conduit and a closed position for interlocking engagement about the tubular conduit. The sleeve means defines at least one needle-receiving aperture and carries self-sealing needle-penetrable means adapted to snugly cushion and fluidly seal the tubular conduit in the closed position. This arrangement permits a needle to be injected through the aperture and the self-sealing means into the tubular conduit without fear of leakage.

In the embodiment shown, the first and second sections are integrally hinged together and define an interior recess communicating with the needle-receiving aperture for snugly receiving the self-sealing needle-penetrable means.

In one embodiment, the sleeve means includes a generally circular barrel of fluid impermeable plastic and the coupling means includes an elongated apertured strap attached to the first section and a lug extending outward from the second section.

In another embodiment the sleeve means includes a tubular barrel and the coupling means includes a set of lugs integrally extending from the first section and a set of lug-receiving sockets extending from the second section.

A more detailed explanation of the invention is provided in the following description and appended claims taken in conjunction with the accompanying drawing.

BRIEF DESCRIPTION OF THE DRAWINGS

FIG. 1 is a perspective view of a clamp-on injection site in accordance with principles of the present invention and shown in a closed position about a tubular conduit;

FIG. 2 is a cross-sectional view thereof, taken substantially along line 2—2 of FIG. 1;

FIG. 3 is an exploded perspective view of the clamp-on injection site in an open position; and FIG. 4 is an exploded perspective view of a modified embodiment of the clamp-on injection site in accordance with principles of the present invention.

DETAILED DESCRIPTION OF THE ILLUSTRATIVE EMBODIMENT

Referring to the drawings, a disposable, portable self-clamping injection site 10 is shown positioned along a flexible needle-penetrable tubular conduit 12, such as a flexible vinyl transparent-plastic tube. The injection site includes an elongated tubular barrel 14 of fluid-impermeable needle-impenetrable plastic with a generally circular cross-sectional configuration.

The tubular barrel includes first and second sections 16 and 18, respectively, which are pivotally attached to each other by means of an elongated integral hinge 20 positioned along a line parallel to the longitudinal axis of the barrel and interconnected to longitudinal edges 16a and 18a of the sections as well as to adjacent section walls 16b and 18b. Opposite the integral hinge 20 are first and second opposed, unhinged section walls, 16c and 18c, respectively, which are spaced from each other so as to define a mouth 22.

The tubular barrel is shaped to define a pair of diametrically opposed needle-receiving apertures 24 and 26 aligned along the major axis of the barrel. The interior curved walls 16d and 18d of the sections are each shaped to define an interior semicircular recess 28 and 30, respectively, communicating with the needle-receiving apertures.

A hook-shaped lug or bead 32 extends outwardly from the outer exterior curved wall 18e of the second section 18 and is oriented adjacent the second unhinged section wall 18c. An elongated plastic strap 34 has a rectangular configuration with one end 34a attached to the first unhinged section wall 16c along the outer, exterior curved wall 16e of the first section 16. The strap defines therein a rectangular aperture 36 positioned midway between the longitudinal edges of the strap and adjacent the attached end 34a. The rectangular aperture 36 is of a size and dimension for matingly receiving the lug 32. In the embodiment shown in FIG. 3, the strap is of transparent, flexible plastic and includes a set of outwardly-extending ridges 38 opposite the attached end 34a, to facilitate manual grasping of the strap.

A pair of semi-cylindrical self-sealing needle-penetrable sleeve elements 40 and 42 of resilient latex or the like, have outer curved walls 40a and 42a, respectively, snugly fit within the respective semi-circular recesses 28 and 30, so that the inner curved walls 40b and 42b of the sleeve elements project radially inward out of the recesses for snugly cushioning and fluid-sealing the tubular conduit 12.

The injection site 10 is operable between an open position, when the lug 32 is not latched to the apertured strap 34, to a closed position, wherein the lug and apertured strap are in latching interlocking engagement. During the open position, the injection site may be movably positioned along the tubular conduit 12. During the closed position, the barrel 14 and sleeve elements 40 and 42 cooperate to circumferentially enclose and clamp portions of the tubular conduit.

When the injection site 10 is in the closed position, the barrel and sleeve elements are clamped together by the interlocking action of the strap and lug so as to compress the tubular conduit. Once the injection site is clamped about the tubular conduit, a needle may be inserted through the needle-receiving apertures 24 or 26 into the sleeve elements 40 or 42 and into the interior passageway 12a of the tubular conduit 12 so as to inject a fluid therein. Because the injection site forms a fluid seal about the tubular conduit, the needle 44 may be injected and withdrawn from the tube 12, via the injection site, without fear of leakage.

The modified embodiment of the injection site 10' is similar to the injection site shown in FIGS. 1-3, except as herein specified. An oblong, self-sealing needle-penetrable resilient member 46 of latex or the like replaces sleeve elements 40 and 42. Similarly, the interior recess 30' of the barrel is shaped complementarily to the configuration of the oblong member 46 so as to snugly receive the outer wall 46a of the oblong member. When the outer wall 46a is seated in the recess 30', the inner wall 46b of the oblong member projects radially inward out of the inner curved wall 16d' for snugly cushioning and fluidly sealing the tubular conduit. The needle-receiving aperture 24' communicates with the interior recess 30'. Although no limitation is intended, only one oblong member 46 is shown in the modified embodiment of the injection site 10', and the tubular barrel is shown with only one needle-receiving aperture 24' and one recess 30'.

In the modified embodiment, lug 32 is replaced by a set of lugs 48 extending radially outward along the outer curved wall 18e' of the second section 18' to a point above the second unhinged wall 18c'. A set of lug-receiving apertured-sockets 50 extend outwardly from the outer curved wall 16e' of the first bifurcated section 16' adjacent the first unhinged wall 16c' and replace the elongated strap 34 of the first embodiment. The operation of the modified injection site 10' is substantially similar to the injection site 10 of the first embodiment shown in FIGS. 1-3.

Among the many advantages of an injection site 10 and 10' made in accordance with principles of the present invention are:

1. The injection site can be clamped onto the tubing anywhere along the line at any time.

2. The injection site need not be integrally mounted to the tubing at the manufacturing plant, thereby reducing manufacturing costs.

3. The injection site need not be bonded to the tubing during on-site assembly, thereby reducing manufacturing costs and assembly time.

4. The portable injection site avoids creeping and set (bending and twisting) that occurs in vinyl tubing (with bonded, prior art injection sites) when the tubing is compressed and stored for long periods of time.

Although an embodiment of the invention has been shown and described, it is to be understood that various modifications and substitutions may be made by those skilled in the art without departing from the novel spirit and scope of the invention.

What is claimed is:

1. A self-clamping injection site adapted to be positioned along a flexible, needle-penetrable, tubular conduit, comprising:
    a. a sleeve member having a first section and a second section hinged together for moving each of said sections between an open position allowing the sleeve to be positioned along the tubular conduit and a closed position for fixing the sleeve on the conduit at a predetermined position;
    b. said first and second sections defining securing mean for locking said sleeve at said predetermined position;
    c. said sleeve further defining at least one needle receiving aperture for allowing a needle to readily pass therethrough;
    d. said sleeve carrying a self-sealing, needle-penetrable material in said open and said closed position and in communication with said aperture; and
    e. said material being compressed between said sleeve and said conduit by said securing means when said sleeve is in the closed position thereby permitting a needle to be injected through the aperture, the self-sealing material and the tubular conduit.

2. An injection site as in claim 1 wherein the first and second sections are integrally hinged together.

3. An injection site as in claim 1 wherein the sleeve means further defines an interior recess communicating with the needle-receiving aperture for snugly receiving the self-sealing needle-penetrable means.

4. An injection site as in claim 1 wherein the first and second sections are integrally hinged together and define an interior recess communicating with the needle-receiving aperture for receiving the self-sealing needle-penetrable means.

5. An injection site as in claim 1 wherein the coupling means includes a strap integrally extending from the first section and a lug extending outward from the second section, said strap defining an aperture for cooperatively receiving said lug in the closed position.

6. An injection site as in claim 1 wherein the coupling means includes a set of lugs extending outwardly from the second section and a set of female socket members extending outwardly from the first section for matingly snap-fitting engagement with the lugs during the closed position.

7. An injection site as in claim 3 wherein the self-sealing needle-penetrable means includes semi-cylindrical sleeve elements snugly seated in said recess and extending inwardly therefrom for engaging said tubular conduit.

8. An injection site as in claim 1 wherein the self-sealing needle-penetrable means includes an oblong latex member for resiliently abutting said tubular conduit.

9. A self-clamping injection site adapted to be positioned along a flexible needle-penetrable tubular conduit having an annular cross-sectional configuration, comprising in combination:

a barrel of fluid-impermeable needle-impenetrable plastic having first and second sections integrally hinged together and operable between an open position for removable positioning along the tubular conduit and a closed position for interlocking engagement about said tubular conduit, said barrel defining at least one needle-receiving aperture and an interior recess communicating with said aperture and including a lug extending outward from the first section;

an elongated strap operatively attached to the second section and defining a lug-receiving aperture for latching interlocking engagement with said lug so as to clamp the sections together during the closed position; and self-sealing needle-penetrable sleeve means disposed in said recess and extending inwardly therefrom for snugly cushioning and fluid sealing said tubular conduit so as to permit a needle to be injected through the aperture and sleeve elements into said tubular conduit.

10. An injection site as in claim 9 wherein the barrel is generally circular and cooperates with said sleeve elements to compress the contacted portion of the tubular conduit during the closed position.

11. An injection site as in claim 10 wherein the strap includes ridge means to facilitate manually-grasping of said strap.

12. A self-clamping injection site adapted to be positioned along a flexible needle-penetrable tubular conduit, comprising in combination:

a tubular barrel having first and second sections hinged together to provide a mouth operable between an open position for removable positioning along the tubular conduit and a closed position for interlocking engagement about said tubular conduit, said barrel defining a needle-receiving aperture and an interior recess communicating with said aperture and including means for connecting said first section to said second section so as to lock said sections together in the closed position; and a self-sealing needle-penetrable resilient member snugly disposed in said recess and extending inwardly therefrom for cushioning and fluidly sealing said tubular conduit so as to permit fluid-tight injection and withdrawal of a needle through said member and said tubular conduit.

13. A leak-free injection site for use in cooperation with a flexible, fluid-carrying and needle-penetrable, tubular conduit for inserting a needle into and withdrawing the needle from said conduit without interrupting the flow therein, said site comprising:

self-sealing, needle-penetrable material for positioning in sealing engagement with said conduit; and clamp means of sleeve like construction including at least two separable, complementary opposing sections having an open position for positioning said self-sealing material in engagement with said conduit, and a closed position for locking said clamp means in engagement with said conduit, said clamp means including support means therein carrying said self-sealing material in the open and closed position, said clamp means further defining through at least one of said opposing sections needle-access means for exposing at least a portion of said self-sealing material and through which a needle can be inserted into and withdrawn from said self-sealing material and said conduit said clamp means configured to maintain said self-sealing material in sealing engagement with said conduit in said closed position.

14. An injection site as in claim 13, wherein said clamp means includes a plurality of segments constructed to surround said conduit.

15. An injection site as in claim 14, wherein said means for carrying said self-sealing means is a recess associated with at least one of said segments and said segment also includes said needle-access means in needle-penetrating relation with said recess.

16. An injection site as in claim 15, wherein said segments comprise a pair of elongated sleeve-like sections.

17. An injection site as in claim 16, wherein said site further includes: hinge means for interconnecting said sleeve-like sections, said hinge means being positioned along one side of said site; and latch means for securely positioning said sleeve-like sections about said conduit and said self-sealing means in sealing engagement with said conduit.

* * * * *